(12) United States Patent
Veys et al.

(10) Patent No.: US 6,930,098 B2
(45) Date of Patent: Aug. 16, 2005

(54) USE OF POLYSULPHATED CYCLODEXTRINS FOR TREATING OSTEOARTHRITIS

(75) Inventors: Eric Maximilien Veys, Ghent (BE); August Lodewijk Verbruggen, Nazareth (BE)

(73) Assignee: Universiteit Gent, Ghent (BE)

( * ) Notice: Subject to any disclaimer, the term of this patent is extended or adjusted under 35 U.S.C. 154(b) by 0 days.

(21) Appl. No.: 10/333,226

(22) PCT Filed: Jul. 12, 2001

(86) PCT No.: PCT/FR01/02253

§ 371 (c)(1),
(2), (4) Date: Jan. 15, 2003

(87) PCT Pub. No.: WO02/05826

PCT Pub. Date: Jan. 24, 2002

(65) Prior Publication Data

US 2003/0109493 A1 Jun. 12, 2003

(30) Foreign Application Priority Data

Jul. 12, 2000 (FR) .............................. 00 09272

(51) Int. Cl.$^7$ .................. A61K 31/715; A61K 9/14; A61K 31/74; A61K 47/48
(52) U.S. Cl. .................. 514/58; 424/484; 424/486; 424/78.08; 424/78.17
(58) Field of Search .................. 424/484, 486, 424/78.08, 78.17; 514/58

(56) References Cited

U.S. PATENT DOCUMENTS

| 4,247,535 | A | | 1/1981 | Lewis et al. |
| 4,258,180 | A | | 3/1981 | Lewis et al. |
| 5,843,920 | A | * | 12/1998 | Weisz ......................... 514/58 |

FOREIGN PATENT DOCUMENTS

| EP | 0447171 | 9/1991 |
| EP | 0754460 | 1/1997 |
| WO | WO 91/16905 | 11/1991 |
| WO | WO 92/13895 | 8/1992 |
| WO | WO 93/09790 | 5/1993 |

OTHER PUBLICATIONS

Da Camara "Glucosamine Sulfate for Osteoarthritis," *Annals of Pharmacotherapy*, vol. 32, No. 5, May 1998, pp. 580–587.

Hamerman, D. "The Biology of Osteoarthritis," *New England Journal of Medicine*, vol. 320, No. 20, May 18, 1989, pp. 1322–1330.

* cited by examiner

*Primary Examiner*—Thurman K. Page
*Assistant Examiner*—Blessing Fubara
(74) *Attorney, Agent, or Firm*—The Firm of Hueschen and Sage

(57) ABSTRACT

The present invention relates to the method of using polysulphated cyclodextrins or addition salts thereof for use in the treatment of arthrosis, and pharmaceutical compositions thereof.

7 Claims, No Drawings

USE OF POLYSULPHATED CYCLODEXTRINS FOR TREATING OSTEOARTHRITIS

The present invention relates to the use of polysulphated cyclodextrins and of addition salts thereof in obtaining pharmaceutical compositions for use in the treatment of arthrosis.

The therapeutic use of cyclodextrins and synthetic derivatives thereof has been widely studied in the course of the last fifteen years.

The introduction of sulphate groups onto the hydroxy groups of cyclodextrins provides them with especially valuable biological properties. In particular, it has been shown that polysulphated cyclodextrins could reduce, or block, the effects of teratogenic substances on foetal development (WO 9116905), and that they have scar-tissue-forming power (WO 9309790). They are also known as inhibitors of retroviruses, in particular HIV (EP 447 171), and also as inhibitors of angiogenesis (WO 8906536).

The Applicant has now discovered that, surprisingly, polysulphated cyclodextrins and addition salts thereof could be used advantageously in obtaining medicaments for use in the treatment of arthrosis.

Polysulphated cyclodextrins for use according to the invention are polysulphated α-, β- or γ-cyclodextrins.

Among the addition salts of polysulphated cyclodextrins there may be mentioned, without implying any limitation, the salts of sodium, calcium, potassium, ammonium etc.

Arthrosis is characterised anatomically by initial and primary destruction of articular cartilages.

Under normal conditions, the renewal of cartilage is a very slow process consisting of a phase of resorption by chondrocytes which is directly compensated by a phase of formation by those same chondrocytes.

Under pathological conditions, the renewal of cartilage may be accelerated, leading to a premature cartilage repair reaction followed by cellular decompensation and cartilage degradation. The repair reaction results from clonal proliferation of chondrocytes and their increased synthesis of matrix components of the cartilage (D. Hamerman et al., N. Engl. J. Med., 1989, 320(20), 1322–1330). This homeostatic reaction is not adaptive and depends on systemic hormones and growth factors whose secretion decreases with age. Resorption of the cartilage is regulated by enzymes and free radicals produced by adjacent tissues, as well as, especially, by the chondrocyte itself.

In particular, the strength of the cartilage, and its ability to repair itself, is governed by proteoglycans of the extracellular matrix, especially aggrecans. The synthesis of such aggrecans by articular chondrocytes, and their quality, decreases with age, which represents one of the main factors implicated in the development of arthrosis.

More specifically, it has been discovered that polysulphated cyclodextrins stimulate the synthesis of proteoglycans and, more especially, of aggrecan and of aggregates thereof by human articular cartilage cells.

This has been confirmed by measurement of $^{35}S$ incorporated in the aggrecan network by chondrocytes and by an increase in the levels of aggrecans having, as a consequence, an increase in the synthesis of aggrecan in the pericellular matrix.

The therapeutic use of polysulphated cyclodextrins is all the more promising because these compounds, in contrast to other polysaccharides, have well-defined structures. Their molecular weight is lower that that of polysulphated polysaccharides used therapeutically, such as chondroitin sulphate and chondroitin polysulphate, certain toxic effects of which, after parenteral administration, have been attributed to their high molecular weight.

The biological effects of such polysulphated cyclodextrins are, moreover, greater than those of the above-mentioned polysulphated polysaccharides.

Polysulphated cyclodextrins are prepared by reacting chlorosulphonic acid with the cyclodextrins, in accordance with the method described by T. Astrup. et al. (Acta Phys. Scand., 1944, 8, 215–226).

The pharmaceutical compositions according to the invention will be presented in forms suitable for administration by the oral, parenteral, transcutaneous, nasal, rectal and perlingual routes, and especially in the form of injectable preparations, tablets, sublingual tablets, glossettes, soft gelatin capsules, hard gelatin capsules, lozenges, suppositories, creams, ointments, dermal gels etc.

In addition to comprising an appropriate amount of polysulphated cyclodextrin, the compositions according to the invention comprise one or more pharmaceutically inert excipients or carriers selected, especially, from diluents, lubricants, binders, disintegrating agents, absorbents, colourants, sweeteners etc.

By way of example, and without implying any limitation, there may be mentioned:

as diluents: lactose, dextrose, sucrose, mannitol, sorbitol, cellulose, glycerol, as lubricants: silica, talc, stearic acid and magnesium and calcium salts thereof, polyethylene glycol, as binders: aluminium silicate, magnesium silicate, starch, gelatin, tragacanth, methylcellulose, carboxymethylcellulose and polyvinylpyrrolidone, as disintegrants: agar, alginic acid and its sodium salt, effervescent mixtures.

The useful dosage varies according to the sex, age and weight of the patient, the administration route, the nature of the condition and of any associated treatments, and ranges from 50 mg to 1500 mg per 24 hours in one or more administrations.

Preparation of Polysulphated Cyclodextrins in the Form of Sodium Salts 300 mg of cyclodextrin are added to 5 ml of a solution prepared by addition of one volume of chlorosulphonic acid to 6.6 volumes of pyridine at 0° C. The solution thereby obtained is held at 100° C. for 5 days. After cooling and addition of 25 ml of water and then of 100 ml of a 10% solution of sodium acetate in methanol, the precipitate formed is filtered off and washed with methanol. The precipitate is then dissolved in water and is subsequently eluted by chromatography on a gel-permeation column to yield the expected polysulphated cyclodextrin, which is then lyophilised. The degree of sulphatation of the cyclodextrin is determined by electrophoresis or by mass spectrometry. Under these conditions, the sulphatation of the cyclodextrins is complete.

EXAMPLE 1

Pharmacological Study

The studies were carried out using polysulphated α-, β- and γ-cyclodextrins in the form of sodium salts.

Evaluation of the in vitro effects of polysulphated cyclodextrins on the synthesis of extracellular aggrecans by chondrocytes.

Materials and Methods

Human articular chondrocytes are isolated according to the methods described by W. T. Green Jr (Clin. Orthop., 1971, 75, 248–260) and K. E. Kuettner et al. (J. Cell. Biol., 1982, 93, 743–750).

The chondrocytes are then cultured in agarose gel, in accordance with the method described by P. D. Benya et al. (Cell., 1982, 30, 215–224) and modified according to M. Cornelissen et al. (J. Tiss. Cult. Meth., 1993, 15, 139–146) and according to G. Verbruggen et al. (Clin. Exp. Rheumatol, 1990, 8, 371–378).

Synthesis of aggrecans: This is measured by determining the incorporation of 35S, supplied by a radioactive precursor, sodium sulphate $Na_2{}^{35}SO_4$. After culturing for two weeks, 10 μCi/ml of the radio-labelled precursor are introduced into the culture medium for 48 hours, as well as the compounds under test (polysulphated α-, β- and γ-cyclodextrins) or the reference compounds (chondroitin sulphate and polysulphate) at an end concentration of 2.5 μg/ml.

The newly synthesised $^{35}S$-aggrecans accumulate partly in the intercellular agarose medium or are released into the incubation medium.

At the end of the incubation period, the agarose gel is broken up mechanically and is then digested with 3 ml of a 50 U/ml solution of agarose in a 0.067M phosphate buffer at pH 6.0, in the presence of proteinase inhibitors.

The suspension thereby obtained is centrifuged; the supernatant, which comprises the $^{35}S$-aggrecans of the interterritorial matrix, and the incubation medium, comprising the metabolites of $^{35}S$-aggrecans released into the extracellular matrix, are combined for subsequent chromatography.

The centrifuged pellet, comprising the chondrocytes and the $^{35}S$-aggrecans associated therewith, is treated for 48 hours with 1 ml of a 4.0M solution of guanidinium chloride in a 0.05M acetate buffer at pH 5.8 comprising the proteinase inhibitors. The objective of this operation is to extract the $^{35}S$-aggrecans associated with the cells. The solution obtained is centrifuged to separate the cells from the supernatant, which is separated off for subsequent chromatography. The chromatography operations on the various fractions obtained are carried out on Sephadex G25 gel in a pH 6.8 phosphate buffer containing 0.01M $Na_2SO_4$, so as to separate the $^{35}S$-aggrecans from the free $Na_2{}^{35}SO_4$.

The radioactivity of each of the macromolecular eluates obtained is measured and related to the number of chondrocytes contained in the initial culture and is expressed in terms of pg of $SO_4$ incorporated into the aggrecans, per million chondrocytes and per hour.

Results

The results are summarised in the Table below.

| Compounds tested* (2.5 μg/ml) | Amount of $^{35}S$-aggrecans | | |
| --- | --- | --- | --- |
| | associated with the cells | in the interterritorial matrix | in the medium |
| α CD | 1315 | 8036 | 1589 |
| β CD | 2262 | 6232 | 1658 |
| γ CD | 2907 | 8232 | 3873 |
| CS | 1373 | 6589 | 2187 |
| CPS | 1392 | 6446 | 2519 |
| Control | 897 | 5527 | 2318 |

*α CD = polysulphated α-cyclodextrin, β CD = polysulphate β-cyclodextrin, γ CD = polysulphated γ-cyclodextrin, CS = chondroitin sulphate, CPS = chondroitin polysulphate The Table shows the remarkable effectiveness of the polysulphated cyclodextrins, which exceeds that of the reference compounds both in terms of the production of cell-associated aggrecans and in terms of aggrecans present in the interterritorial matrix, which is a consequence thereof.

In all cases, the results obtained, both for the compounds of the invention and for the reference compounds, exceed those obtained for the control group.

EXAMPLE 2

Pharmaceutical Composition

Tablets Containing 100 mg of Polysulphated γ-Cyclodextrin Sodium Salt

| Formula for the preparation of 1000 tablets | |
| --- | --- |
| polysulphated γ-cyclodextrin sodium salt | 100 g |
| Hydroxypropylcellulose | 2 g |
| Wheat starch | 10 g |
| Lactose | 100 g |
| Magnesium stearate | 3 g |
| Talc | 3 g. |

What is claimed is:

1. A method of treating a living animal body, including a human, afflicted with arthrosis comprising the step of administering to the living animal body, including a human, a composition consisting essentially of a polysulphated cyclodextrin or an addition salt thereof, in combination with one or more non-toxic pharmaceutically acceptable excipients, for treatment of the condition.

2. The method of claim 1, wherein the polysulphated cyclodextrin is polysulphated γ-cyclodextrin or an addition salt thereof.

3. The method of claim 1, wherein the polysulphated cyclodextrin is polysulphated α-cyclodextrin or an addition salt thereof.

4. The method of claim 1, wherein the polysulphated cyclodextrin is polysulphated β-cyclodextrin or an addition salt thereof.

5. The method of claim 1, wherein the dosage of the polysulphated cyclodextrin or addition salt thereof ranges from 50 mg to 1,500 mg per 24 hours.

6. The method of claim 1, wherein the non-toxic pharmaceutically acceptable carrier is selected from the group consisting of diluents, lubricants, binders, disintegrating agents, absorbents, colorants, and sweeteners.

7. The method of claim 1, wherein administration of the composition is effected in the form of an injectable preparation.

* * * * *

UNITED STATES PATENT AND TRADEMARK OFFICE
CERTIFICATE OF CORRECTION

PATENT NO. : 6,930,098 B2  Page 1 of 1
DATED : August 16, 2005
INVENTOR(S) : Eric Maximilien Veys et al.

It is certified that error appears in the above-identified patent and that said Letters Patent is hereby corrected as shown below:

Title page,
Item [75], Inventors, "Ghent" should be -- Gent --.
Item [73], Assignee, "Ghent" should be -- Gent --.

Signed and Sealed this

First Day of November, 2005

JON W. DUDAS
*Director of the United States Patent and Trademark Office*